United States Patent [19]

Houghton et al.

[11] Patent Number: 5,104,652
[45] Date of Patent: Apr. 14, 1992

[54] COMPOSITIONS AND METHOD FOR TREATMENT OF CANCER USING MONOCLONAL ANTIBODY AGAINST $G_{D3}$ GANGLIOSIDE TOGETHER WITH IL-2

[75] Inventors: Alan N. Houghton; Karl Welte, both of New York; Glenn Miller, Port Washington; Paul Chapman; Lloyd J. Old, both of New York, all of N.Y.

[73] Assignee: Sloan-Kettering Institute for Cancer Research, New York, N.Y.

[21] Appl. No.: 549,238

[22] Filed: Jul. 5, 1990

Related U.S. Application Data

[63] Continuation of Ser. No. 395,210, Aug. 16, 1989, abandoned, which is a continuation of Ser. No. 930,292, Nov. 13, 1986, abandoned.

[51] Int. Cl.$^5$ .................. A61K 37/02; A61K 39/00; C12N 5/02
[52] U.S. Cl. .................. 424/85.2; 424/85.1; 424/85.8; 435/240.2; 435/240.21; 435/240.25
[58] Field of Search .................. 424/85.1, 85.2, 85.8; 435/240.2, 240.21, 240.25

[56] References Cited

U.S. PATENT DOCUMENTS 4,507,391 3/1985 Pukel et al. .................. 435/68
4,844,893 7/1989 Honsuk et al. .................. 530/387

FOREIGN PATENT DOCUMENTS 0173648 3/1986 European Pat. Off. .
0211368 2/1987 European Pat. Off. .
WO86/00909 2/1986 PCT Int'l Appl. .................. 435/240

OTHER PUBLICATIONS

Kasugi et al., Jpn, I Cancer Chemother. 11(8) 1984, pp. 1527-1537 (English translation).
Hersey et al., Cancer Res., 12/86, vol. 46, pp. 6083-6090.
Honsik et al., PNAS, 10/86, pp. 7893-7897, vol. 83.
Hersey et al., Australian & New Zealand J. of Medicine (Feb. 1986) vol. 16:152.

Primary Examiner—Garnette D. Draper
Attorney, Agent, or Firm—John P. White; Antoinette Konski

[57] ABSTRACT

Cell surface gangliosides are presumed to play a role in cell growth and differentiation. Using monoclonal antibodies directed against $G_{D3}$, a disialoganglioside expressed predominantly by cells of neuroectodermal origin, we have found that $G_{D3}$ is expressed by a subpopulation of cells of the immune system including: a) fetal thymocytes in subcortical regions and near vessels, 2) lymph node lymphocytes in interfollicular areas and near vessels, and 3) a small subset of T cells in the peripheral blood. Mouse monoclonal antibodies (two IgGs, one IgM and F(ab')$_2$ fragments) reacting with $G_{D3}$ were found to stimulate proliferation of T cells derived from peripheral blood. Proliferation induced by binding to $G_{D3}$ could be augmented by exogenous IL-2, PMA, PHA or Protein A.

9 Claims, 12 Drawing Sheets

| FIG. 1a | FIG. 1b |
|---------|---------|
| FIG. 1c. | FIG. 1d |

COMPOSITIONS AND METHOD FOR TREATMENT OF CANCER USING MONOCLONAL ANTIBODY AGAINST $G_{D3}$ GANGLIOSIDE TOGETHER WITH IL-2

This work was performed in part with U.S. government funding under grants from the National Cancer Institute (CA 23766, CA33484, CA 33049). Therefore, the United States Government has certain rights in this invention.

This is a continuation of application Ser. No. 395,210, filed Aug. 16, 1989, abandoned, which is a continuation of application Ser. No. 930,292, filed Nov. 13, 1986, now abandoned.

SUMMARY

Monoclonal antibody, or its F(ab')$_2$ portion, specific for $G_{D3}$ ganglioside stimulates lymphocyte proliferation in human T cells. The effect also shows induction of IL-2 receptors and IL-2 secretion by lymphocytes as well as an increase in the percent of $G_{D3}{}^+$ cells. This T-cell stimulation effect is augmented by exogeneous IL-2, PHA and PMA.

DESCRIPTION

Detailed Description of the Drawings

FIG. 1a–1d

Immunofluorescence staining of fetal thymus (a-c) and adult lymph node (d) with mAb R24. MAb R24 reacts with thymocytes in subcortical areas (a), around blood vessels (b), and near Hassal's corpuscles (c). MAb R24 stains patches of lymphocytes in paracortical areas (d). Original magnification, x 200.

FIG. 2a and 2b

Thin layer chromatography and densitometric scanning of ganglioside preparations. a) $E^{30}$ cells were stimulated with mAb R24 (100 ug/mL) for 5 days (ug=microgram). Melanoma (MEL) ganglioside preparation was prepared from a fresh melanoma metastatic tumor from an axillary lymph node. b) Densitometric scanning of the thin layer chromatography in a) ———, scanning of ganglioside preparation of E+ cells; ———, gscanning of $G_{D3}$ standard lane. Arrow designates $G_{D3}$ peak.

FIG. 3

Inhibition by purified gangliosides of mAb R24 reactivity against a ganglioside preparation from unstimulated E+ cells. Bars represent one standard deviation.

FIG. 4

Time course of proliferation of E+ lymphocytes in the presence (•) or absence (o) of mAb R24 (100 ug/ml). Proliferation was measured by $^3$H-thymidine uptake as described below. The results are presented as median and 100% range of 3 independent experiments (Range and standard deviation of $^3$H-thymidine uptake of medium controls was within 10% of median values).

Figure 5A:
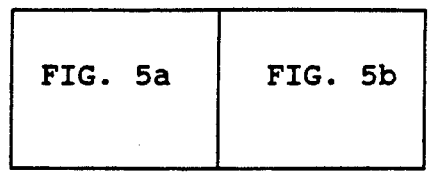
FIGS. 5a and 5b shows the mitogenic effect of different concentrations of R24.
Figure 5A:
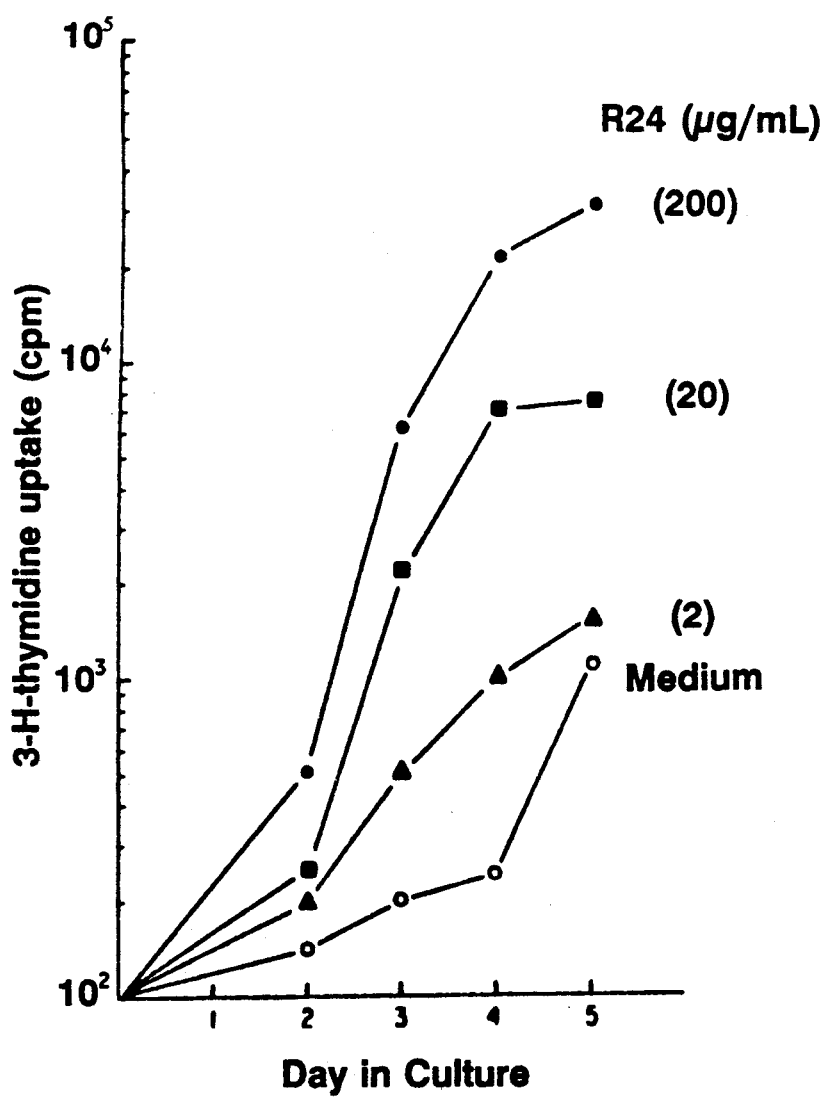
Figure 5B:
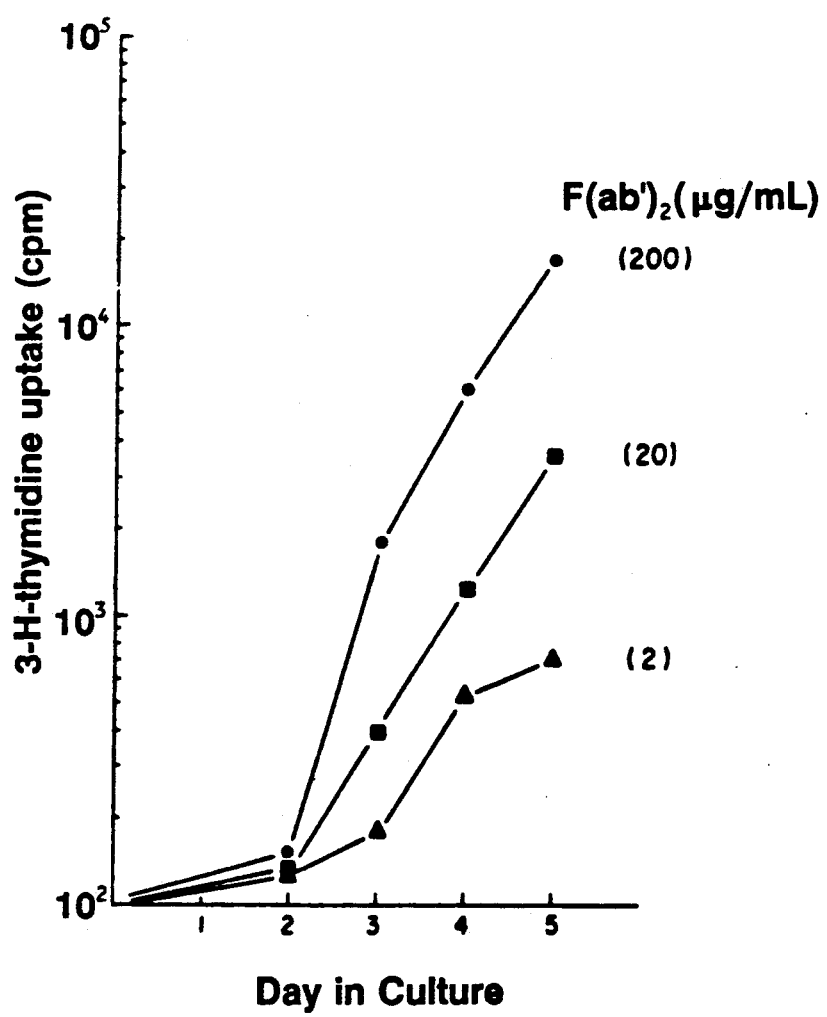

FIGS. 5a and 5b

Mitogenic effect of different concentrations of mAb R24 (FIG. 5a) or F(ab')$_2$ fragments of mAb R24 (FIG. 5b). The results are shown as $^3$H-thymidine uptake for days 1-5 of culture. Each point represents the medium of triplicate cultures. The 100% range was within 15% of the median. FIG. 5a shows the proliferation of E+ cells in the absence of antibodies (medium control). The concentrations of mAb R24 or F(ab')$_2$ fragments of mAb R24 are shown in the Figure: (200)=200 ug/mL; (20)=20 ug/mL; (2)=2 ug/mL.

FIG. 6

Flow-cytometer analysis of E+ cells stimulated with anti-CD3 (OKT-3) antibody (2.5 ng/mL) or mAb R24 (100 ug/mL). E+ cells at initiation of cultures (day 0) or day 5 of cultures were incubated with mAb R24 (10 ug/10$^6$ cells) followed by incubation with FITC-labeled goat-anti-mouse immunoglobulin (GAMIg FITC). Cells were analyzed by a FACS IV. A: MAb R24+GAMIg FITC staining of anti-CD3 (OKT-3) stimulated cultures (18% R24+ cells) (day 5) or staining with GAMIg FITC alone (control). B: Fluorescence intensity of E+ cells stained with mAb R$^{24}$+GAMIg FITC at day 0 (9.9% R$^{24}$+cells) and day 5 (44% R24+ cells) of culture. Fluorescence intensity is shown on a logarithmic scale.

FIG. 7

Effects of PHA, anti-T cell monoclonal antibodies (anti-CD2, anti-CD3, anti-CD8) and PMA on mAb R24 induced proliferation of E+ cells. The proliferation induced by mAb R24 alone as measured by $^3$H-thymidine uptake is shown as 100% and corresponds to 63426±4729 cpm. The concentrations of mAb R24 wa 100 ug/mL, PHA 1% (v/v), OKT-3 250 ng/mL, OKT-11 1ug/mL, OKT-8 1ug/mL, PMA 5 ng/mL. Proliferation was measured at day 5 in culture. Results of experiments performed at days 3 and 7 of culture showed the same pattern as day 5 experiments.

Gangliosides are a class of glycosphingolipids that contain sialylated oligosccharide groups attached to a lipid core structure. Although the exact function of gangliosides is not known, it has been suggested that they play a role in cell signaling and recognition (Hakomori, S., (1981) Ann. Rev. Biochem. 50:733; Yu, R. K., et al. (1984) Adv. Exp. Med. Biol. 174:87). Specific gangliosides have been implicated as receptors for viruses (Markwell, M. A. K., et al. (1981) Proc. Natl. Acad. Sci. USA 78:5406; Bergelson, L. D., et al. Eur. J. Biochem. 128:467 (1982); Suzuki, Y., et al. (1985) J. Biol. Chem. 260:1362) and toxins (Fishman, P. H., (1982) J. Membr. Biol. 69:85). Other evidence has suggested that gangliosides can modify growth factor receptor functions and alter the affinity of these receptors (Bremer, E. G., et al. (1984) J. Biol. Chem. 259:6818; Bremer, E. G., et al. (1986) J. Biol. Chem. 261:2434; Lacetti, P., et al. (1984) Adv. Exp. Med. Biol. 174:355). Particular attention has been paid to the relationship of gangliosides and the growth and differentiation of cells of neuroectodermal origin. For instance, gangliosides can induce neural cell proliferation, increase neurite formation (Ferrari, G., et al. (1983) Brain Res. 284:215; Tsuji, S., et al. (1983) J. Biochem. (Tokyo) 94:303; Nakajuma, J., et al. (1986) Biochim. Biophys. Acta.

876:65) and facilitate adhesion of neural cells (Blackburn, C. C., et al. (1986) J. Biol. Chem. 261:2873).

Experimental evidence has suggested that gangliosides and antibodies directed against gangliosides can also influence cells of the immune system (Marcus, D. M. (1984) Mol. Immunol. 21:1083; Whisler, R. L., et al. (1980) J. Immunol. 125:2106; Merritt, W. D., et al. (1984) Cell. Immunol. 89:1). Recent reports have demonstrated that binding of the B subunit of cholera toxin to cell surface $G_{M1}$ can induce proliferation of rat thymocytes (Spiegel, S., et al. (1985) Science 230:1285) and that monoclonal antibodies directed against the disialoganglioside $G_{D3}$ can enhance the response of lymphocytes to mitogens (Hersey, P., et al. (1986) Aust. NZ. J. Med. 16:152). Since these results suggested that binding to specific gangliosides can modulate the growth of lymphocytic cells, we evaluated the effect on lymphoid cells of monoclonal antibodies to $G_{D2}$, $G_{D3}$ and $G_{M2}$ gangliosides. Previous work has shown that monoclonal antibodies against these gangliosides react mainly with cell types derived from the neuroectoderm (Real, F. X., et al. (1985) Cancer Res. 45:4401; Saito, M., et al. (1985) Biochem. Biophys. Res. Comm. 127:1;Natoli, E., et al. (1986) Cancer Res. 46:4116). In the present study, we demonstrate that antibodies to $G_{D3}$ also react with a subset of human fetal thymocytes and with subpopulations of lymphocytes in lymph nodes and peripheral blood. Polyvalent binding of anti-$G_{D3}$ monoclonal antibodies and F(ab')$_2$ fragments to T lymphocytes activates a $G_{D3}$-positive subpopulation of cells, inducing IL-2 production, expression of receptors for IL-2, and cell proliferation. The examples below serve to illustrate the invention without limiting the invention to the specific examples shown. Equivalents of the invention are contemplated as well within the invention.

MATERIALS AND METHODS

Monoclonal Antibodies and IL-2

Hybridoma M-18 (R24) is deposited with the American Type Culture Collection (ATCC) under Accession No. HB 8445.

Mouse monoclonal antibodies (mAB) R24 (IgG3), C5 (IgG3) and K9 (IgM) have been shown to react with $G_{D3}$ (Dippold, W., et al. (1980) Proc. Natl. Acad. SCI. USA 77:6114; Pukel, C., et al. (1982) J. Exp. Med. 155:1133). Mouse mAb 3F8 (IgG3) (a gift from Dr. Nai-Kong Cheung, Case-Western Reserve University, Cleveland, Ohio) recognizes $G_{D2}$ ganglioside (Saito, M., et al. (1985) Biochem. Biophys. Res. Comm. 127:1), mouse mAb 10-11 (IgM) recognizes $G_{M2}$ (Natoli, E., et al. (1986) Cancer Res. 46:4116), and mouse mAb F36/22 (IgG3) reacts with a high molecular weight cell surface glycoprotein expressed by breast carcinoma cells but not by lymphoid cells (Papsidero, L. D., et al. (1984) Cancer Res. 44:4653). MAb R24 was used as hybridoma supernatant or prepared from ascites of mice bearing hybridoma tumors. Preparations of mAbs R24, 3F8, C5 and F36/22 from ascites were purified by precipitation with a saturated ammonium sulfate solution added to a final concentration of 35% (w/v). For further purification, IgG3 antibody preparations were applied to a protein A Sepharose (Pharmacia, Inc., Piscataway, N.J.) column and eluted with 0.5 M citrate/0.15 M NaCl, pH 4.0, buffer. Eluted protein fractions were run through a Sephadex G25 M (Pharmacia, Inc.) column and eluted with phosphate buffered saline (PBS), pH 6.0.

Monoclonal antibodies OKT-3, OKT-4, OKT-6, OKT-8, and OKT-11, either unconjugated or conjugated with FITC, were purchased from Ortho Diagnostics Systems (Raritan, N.J.). OKT-3, OKT-8 and OKT-11 antibodies were extensively dialyzed before use in the proliferation assays. Anti-IL-2 receptor monoclonal antibody labeled with FITC and Leu-2a, Leu-3a and Leu-4 conjugated to phycoerythrin (PE) were purchased from Becton-Dickinson, Inc., Mountainview, Calif. Recombinant IL-2 was kindly provided by Cetus (Emeryville, Calif.)

Production of F(ab')$_2$ Fragments

Purified mAbs R24 or 3F8 in 0.05 M sodium citrate/0.15 M sodium chloride, pH 4.0, were digested with pepsin at 37° C. for 5 min. Pepsin was used in an amount to yield an enzyme:antibody ratio of 1:33 by weight. The reaction was stopped by adding one-third volume 3 M Tris, pH 8.6. The digest was eluted over a protein A Sepharose column (Pharmacia, Inc.) previously equilibrated with PBS, pH 7.0. The F(ab')$_2$ fragments were collected and stored at 4° C. Gel electrophoresis with sodium dodecyl sulfate/polyacrylamide (SDS-PAGE) under non-reducing conditions revealed a single band of 122,000 daltons. Immunofluorescence staining of a panel of R24-positive and -negative cell lines (11 R24+ melanomas and 11 R24− carcinomas) confirmed that the specificity of the R24 F(ab')$_2$ preparation was the same as whole R24 IgG.

Staining of Normal Tissues

Histologically normal adult human lymph nodes were obtained from surgical pathology specimens of patients without cancer within 1-2 hrs after resection. Specimens of fetal thymus were obtained from elective abortions. Fetal gestational age was determined by crown-rump, crown-hell and weight measurements. Tissues were immersed in isopenthane pre-cooled in liquid nitrogen, embedded in OCT compound in cryomolds (Miles Labs, Inc., Naperville, Ill.) and stored at −70° C.

Cryostat-cut tissue sections (4-8 microns thick) were used unfixed or fixed for 10 min with acetone at 4°-8° C. Tissue sections were stained by indirect immunofluorescence or peroxidase methods as previously described (Cordon-Cardo, C., et al. (1986) Int. J. Cancer 37:667). Briefly, tissue sections were incubated in goat (10% v/v) suppressor serum for 20 min, then primary antibody for 1 hr. MAb R24 was used at concentrations between 20-40 ug/mL in the form of hybridoma supernatant or purified mouse ascites. For immunofluorescence staining, sections were then incubated for 45 min with secondary anti-mouse IgG fluorescinated antibody (Cappell Labs, Cochranville, Penna.) and examined with a microscope equipped with epifluorescence and a 100 watt mercury lamp. For immunoperoxidase staining, tissues were quenched with 0.01% $H_2O_2$ in PBS for 10 min, blocked with suppressor serum, and incubated with primary antibody as above. The secondary antibodies were horseradish peroxidase-conjugated (Ortho Diagnostics, Inc., Raritan, N.J.). Diaminobenzidine was used as a chromagen. After staining, sections were counterstained with hematoxylin and mounted.

Mononuclear Cells from Peripheral Blood

Peripheral blood mononuclear cells (PBMC) from human donors were separated by density gradient centrifugation on Ficoll-Hypaque (Boyum, A., (1976)

Scand. J. Immuno. 5(Suppl. 5):9). Cells were washed three times in RPMI 1640 medium supplemented with 2 mM L-glutamine, 50 U/mL penicillin, 50 ug/mL streptomycin, and 10% heat-inactivated fetal bovine serum (FBS). Cells were kept in this medium during all subsequent incubation and washing procedures.

In order to collect adherent cells, up to $3 \times 10^7$ PBMC were incubated 90 min at 37° C. in 5% $CO_2$ in a total volume of 10 mL in Falcon 3003 tissue culture dishes (Falcon Labware Div., Becton-Dickinson, Oxnard, Calif). Nonadherent cells were separated by gently swirling the dishes and slowly pipetting off the medium. Dishes were washed three times with medium, and adherent cells were harvested using a rubber policeman. The adherent cell fraction contained more than 90% monocytes/macrophages as judged by alpha-naphthyl-acetate-esterase stain.

Separation of T Lymphocytes

For isolation of T cells, non-adherent PBMC were rosetted with neuraminidase-treated sheep red blood cells according to a method modified from Weiner et al. (Weiner, M. S., et al. (1973) Blood 42:939). This fraction contained less than 2% monocytes/macrophages and more than 90% of cells reacted with monoclonal antibody OKT-3. THis cell population is designated :"$E^{30}$ cells".

Analysis of Lymphocyte Surface Antigens

For indirect immunofluorescence assays, $10^6$ PBMC in 0.1 mL were incubated with appropriate dilutions of unconjugated monoclonal antibody for 30 min on ice, washed three times in cold PBS/2% bovine serum albumin (BSA), and then incubated on ice with 0.1 mL of a 1:40 dilution of affinity purified goat anti-mouse IgG F(ab')$_2$-FITC (Cappel Lab., Cochranville, Penna.). For two color analyses, cells were washed three more times and incubated with 0.02 mL of PE-labeled monoclonal antibody for 30 min on ice. Cells were washed three times, and adjusted to a concentration of $1 \times 10^6$ cells/mL for analysis by flow cytometry. Background fluorescence was determined by testing with control mouse antibodies (appropriately labeled) instead of test antibody. For direct fluorescence, $10^6$ cells were incubated for 30 min with monoclonal antibody directly conjugated to FITC, washed three times and resuspended for analysis.

Cells were analyzed by flow cytometry using an H-50 Cytofluorograph (Ortho Diagnostic Systems, Inc., Raritan, N.J.) or a FACS IV (Becton-Dickinson). A forward angle scatter versus right-angle green fluorescence cytogram was generated in order to gate around the region of interest (i.e. to differentiate lymphocytic, monocytic and granulocytic cells) and to exclude cell debris and dying cells. When H-50 cytofluorograph was used, an argon-ion laser, tuned to 488 nm around gated regions, was set around lymphocytic cells. From this gated region, green fluorescence (FITC) histograms were generated. For two color fluorescence, green (FITC) versus red (PE) fluorescence was determined and analyzed. A minimum of 10,000 cells were analyzed for each histogram and the per cent positive cells determined by comparison with labeling by control antibody. Data was evaluated using a Data General model 2150 computer system.

Proliferation Assays

Separated PBMC or $E^+$ cells were incubated in triplicate microwell cultures (Costar 3596 plates, Costar, Inc., Cambridge, Mass.) in the presence or absence of mAb R24. Other factors evaluated in proliferation assays included recombinant IL-2 (Cetus Corporation), phytohemmaglutinin (PHA) (Gibco Labs, Grand Island, N.Y.), phorbol-myristate-acetate (PMA) (Sigma Chemicals, St. Louis, Mo.), and protein A (Pharmacia, Inc.). At indicated time points, 100 uL of supernatant were removed from each well to be assayed for IL-2 activity. At specified times, triplicate cultures were pulsed for 4 hours with $^3$H-thymidine (0.5 uCi/well, New England Nuclear, Boston, Mass.) and $^3$H-thymidine uptake was measured as previously described (Welte, K., et al. (1983) J. Immunol. 131:2356).

Assay for IL-2 Activity

For IL-2 assays, a mouse IL-2-dependent cytotoxic T cell line was used as previously described (Welte, K., et al. (1983) supra). One unit of activity in this assay is equivalent to one unit of activity of the IL-2 standard from the Biological Response Modifier program, National Institutes of Health.

Complement-Mediated Lysis of R24-Positive Cells $E^+$ cells were adjusted to a concentration of $10^6$ cells/mL. $E^+$ cells were incubated at room temperature with different concentrations of mAb R24 (100, 10, 1 ug/mL) for one hour, washed and incubated with a complement source (prescreened human serum diluted 1:8 in Veronal buffered medium) at 37° C. for 2 hrs. Cells were washed three times and resuspended for use in proliferation assays. Control cells were treated with PBS followed by complement source alone or with mAb R24 (100 ug/mL) followed by Veronal buffered medium without complement source.

Preparation and Evaluation of Gangliosides $G_{D3}$ was purified from human melanoma tissue and $G_{D2}$ was purified from human brain, as described below. $G_{M1}$ was purchased from Sulpeco, Inc. (Bellafonte, Penna.). $G_{M2}$ was prepared by treatin $G_{M1}$ with beta-galactosidase (from Dr. George W. Jourdian, University of Michigan, Ann Arbor, Mich.) as described by Cahan et al. (Cahan, D. L., et al. (1982) Proc. Natl. Acad. Sci. USA 79:7629). Purity of ganglioside preparations was verified by thin layer chromatography.

Glycolipids were isolated by a modification of the method described by Saito and Kahomori (Saito, T., et al. (1971) J. Lipid Res. 12:257). Briefly, cells were homogenized in chloroform:methanol (C:M) 2:1 and extracted in a 100-fold volume of C:M. The homogenate was filtered and re-extracted twice in C:M, first 1:1, then 1:2. Filtrates were evaporated in a rotary evaporator, acetylated, run through a florisil column, deacetylated and dialyzed against $H_2O$ for 24 hrs. The sample was then re-evaporated and suspended in C:M:$H_2O$ (30:60:8) and applied to a DEAE-Sephadex (Pharmacia, Inc.) column equilibrated with C:M:0.8 M sodium acetate (30:60:8).

For analysis by thin layer chromatography, silica gel plates (Analtech, Newark, Del.) were activated by heating to 100° C. for 1 hr. N-propanol:ammonium hydroxide:$H_2O$ (60:95:11.4) was used to develop chromatographs. After the solvent had migrated 12 cm from the origin, plates were air-dried, baked 10 min at 120° C., cooled to room temperature and sprayed with resorcinol-HCl. Densitometry was evaluated using a Shimadzu CS-930 thin layer chromatography scanner (Kyoto, Japan).

Enzyme-Linked Immunoassay for mAb Reactivity with Gangliosides

Ganglioside preparations from $E^+$ cells were applied to microtest plates (Bellco Glass, Inc., Vineland, N.J.). The plates were air-dried for two hrs and blocked with 1% BSA for two hrs. MAb R24 20 ug/mL was incubated with various concentrations of ganglioside preparations for two hrs and then added to Microtest wells and incubated for one hr at room temperature. Plates were washed three times and incubated for 45 min with anti-mouse IgG conjugated to alkaline phosphatase (Sigma Chemical Corp., St. Louis, Mo.) diluted 1:200. Plates were washed and incubated with diethanolamine substrate for 20 min at 37° C. Reactivity was evaluated on an Artec Systems Corp. model 210 reader (Farmingdale, N.J.).

Radioimmunoprecipitation and Western Blotting

MAb R24 was tested for its ability to react with protein or glycoprotein antigens of unstimulated $E^+$ cells or $E^+$ cells stimulated with mAb R24 (100 ug/mL). Extracts were prepared from detergent solubilized $E^+$ cells (in 0.5% NP-40, 0.01 M Tris, pH 7.5, 0.15 M NaCl and 2 mM $MgCl_2$) or from sonicated extracts of membrane preparations solubilized in 2% (w/v) SDS. Extracts were labeled with $^{125}I$ by the chloramine T method (Greenwood, F. C., et al. (1963) Biochem. J. 89:114). MAb R24, anti-HLA A,B,C antibody W6/32 (Barnstable, C. J., et al. (1978) Cell 14:9), OKT-3 or control antisera (normal mouse serum) was incubated with labeled extracts for 1 hr and rabbit anti-mouse Ig overnight at 4° C. followed by immunoprecipitation with protein A Sepharose (Pharmacia, Inc.), as previously described (Lloyd, K.O., et al. (1981) J. Immunol. 126:2408). Immunoprecipitates were eluted with 2% SDS and analyzed on 9% gels by SDS/PAGE.

Western blotting was performed as described (Towbin, H., et al. (1979) Proc. Natl. Acad. Sci. USA 76:4350). Extracts were separated by SDS/PAGE and transferred to nitrocellulose (Schleicher and Schuell, Keene, NH) or Zeta Probe (BioRad Labs, Richmond, Calif.) membranes for 1.5-3 hrs at 70 V (230 mA) with cooling. Membranes were dried, incubated with mAb R24 followed by goat anti-mouse Ig labeled with horseradish peroxidase and developed with diaminobenzidine/$H_2O_2$.

The following examples serve to illustrate the invention and are not meant to limit the invention to the specific examples shown.

EXAMPLE I

MAb R24 Reacts with Thymocytes and Lymphocytes

Figure 1A:
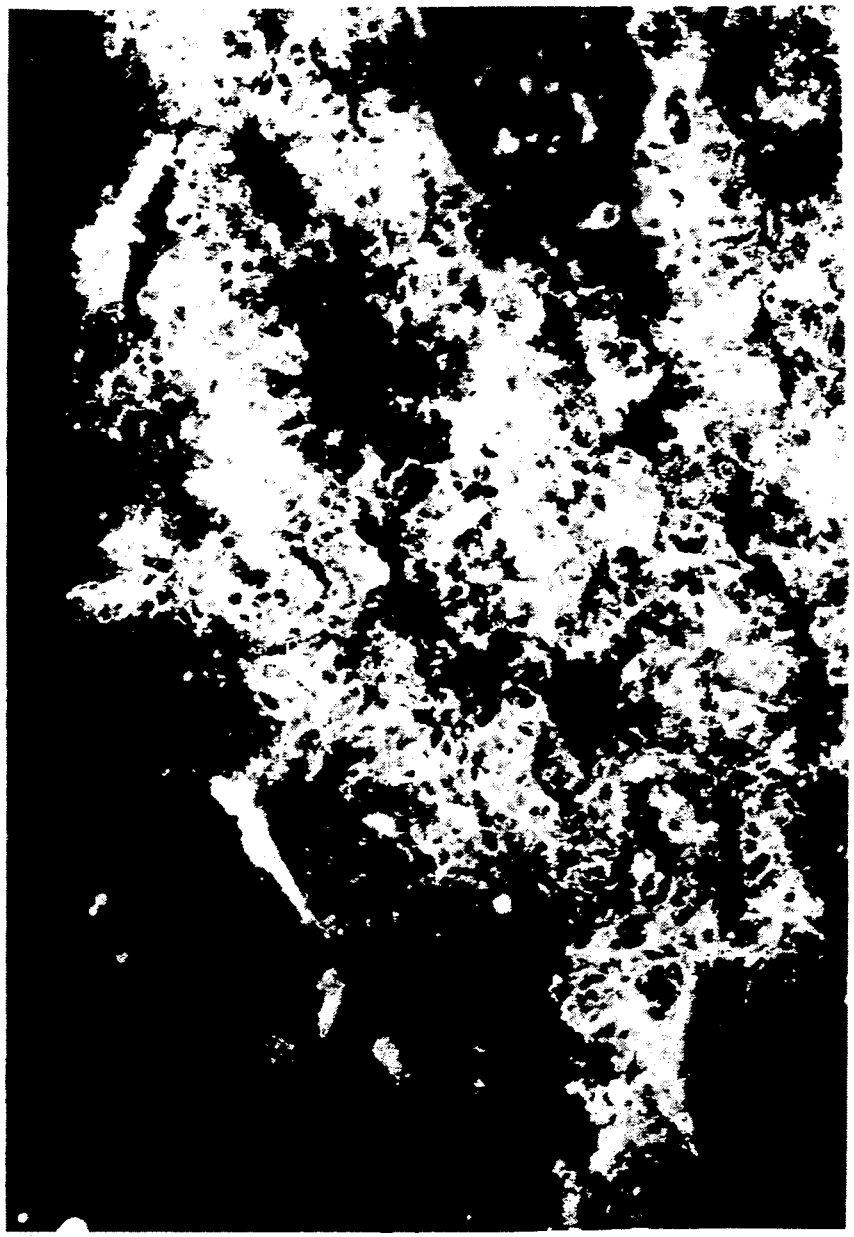
FIG. 1a–1d shows R24 staining of thymocytes, fetal thymus, adult lymph node and lymphocytes.
Figure 1B:
Figure 1C:
Figure 1D:

Mab R24 was found to react with subpopulations of cells in thymus tissues from three 12-14 week old-fetuses. R24+ thymocytes were localized in subcortical areas and in patches around blood vessels and Hassal's corpuscles (FIG. 1a-c). Identical results were observed in tissues stained by immunofluorescence and immunoperoxidase techniques. In order to confirm that mAb R24 was reacting with thymocytes, consecutive 4 micron sections were stained with mAbs R24 or OKT-6; R24+ cells were shown to react with the thymocyte marker OKT-6. In lymph nodes derived from two healthy adults, mAb R24 stained small clusters of lymphocytes around blood vessels in interfollicular and pericortical areas (FIG. 1d).

MAb R24 reacted with 13.9±5.5% (standard deviation, S. D.) of PBMC from 13 healthy individuals (range 7.4-24.3% R24 positive cells). Analysis by two-color flow cytometry to PBMC showed that mAB R24 reacted with a subpopulation of T lymphocytes. In resting T cells derived from peripheral blood of 13 healthy persons, mAb R24 reacted with 14.8±5.7% (S.D.) of CD3+ cells (range 5.0-25.5%), with 20.1±11.7% (S.D.) of CD8+ cells (range 7.0-44.0%) and with 14.0±6.7% (S.D.) of CD4+ T cells (range 6.0-29.7%).

EXAMPLE II

MAb R24 Reacts with $G_{D3}$ Ganglioside on T Lymphocytes

Figure 2A:
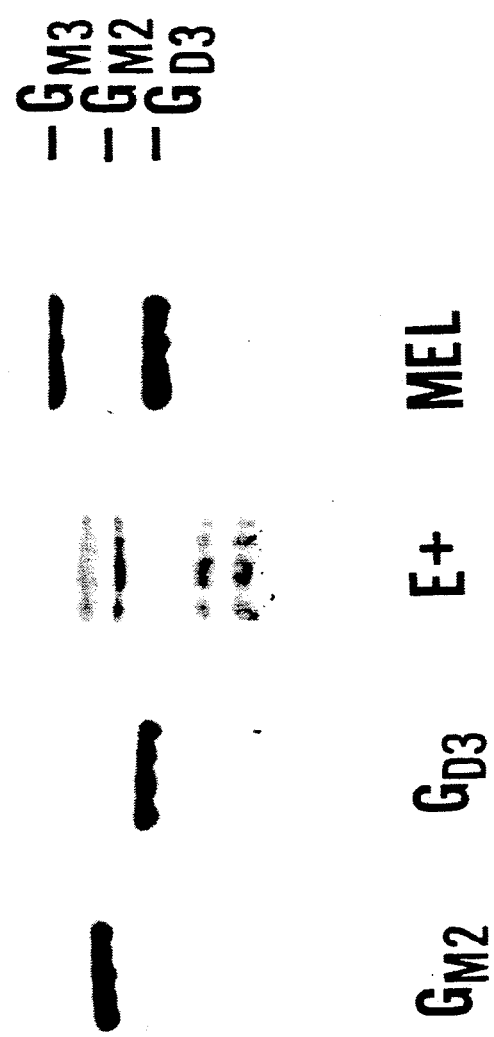
FIGS. 2a and 2b shows thin layer chromatography and densitometric scanning of ganglioside preparations.
Figure 2B:
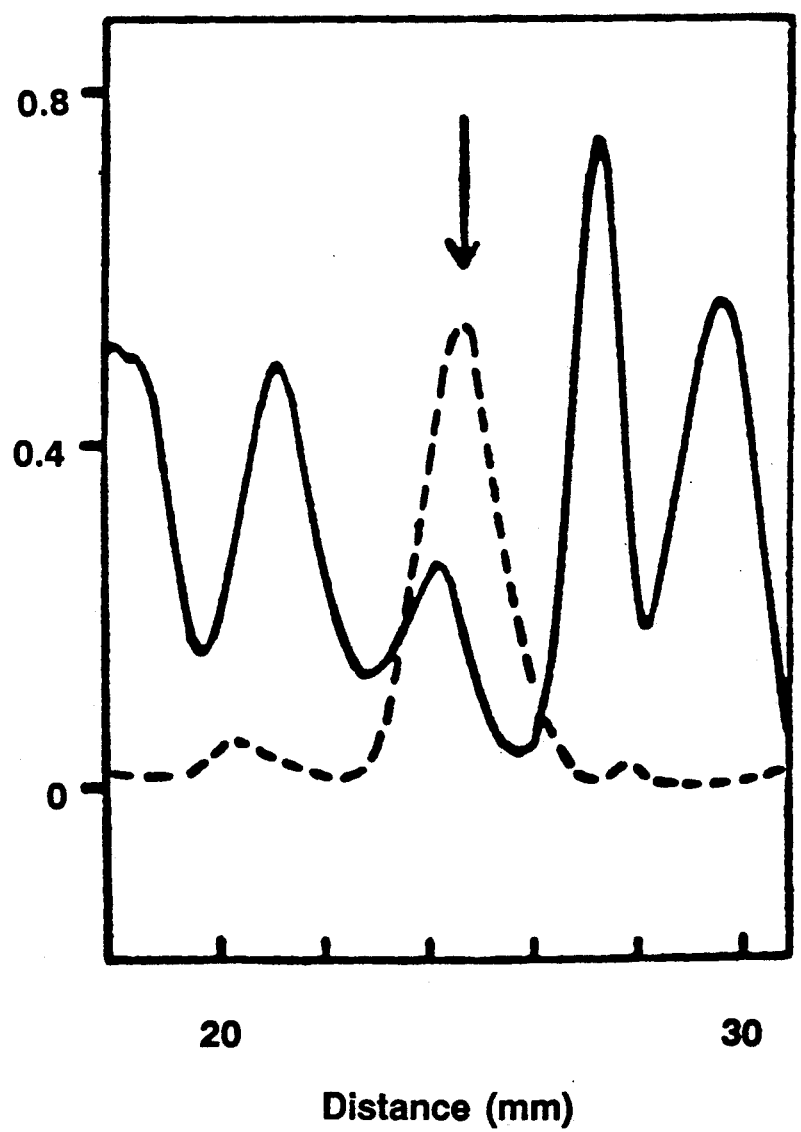
Figure 3:
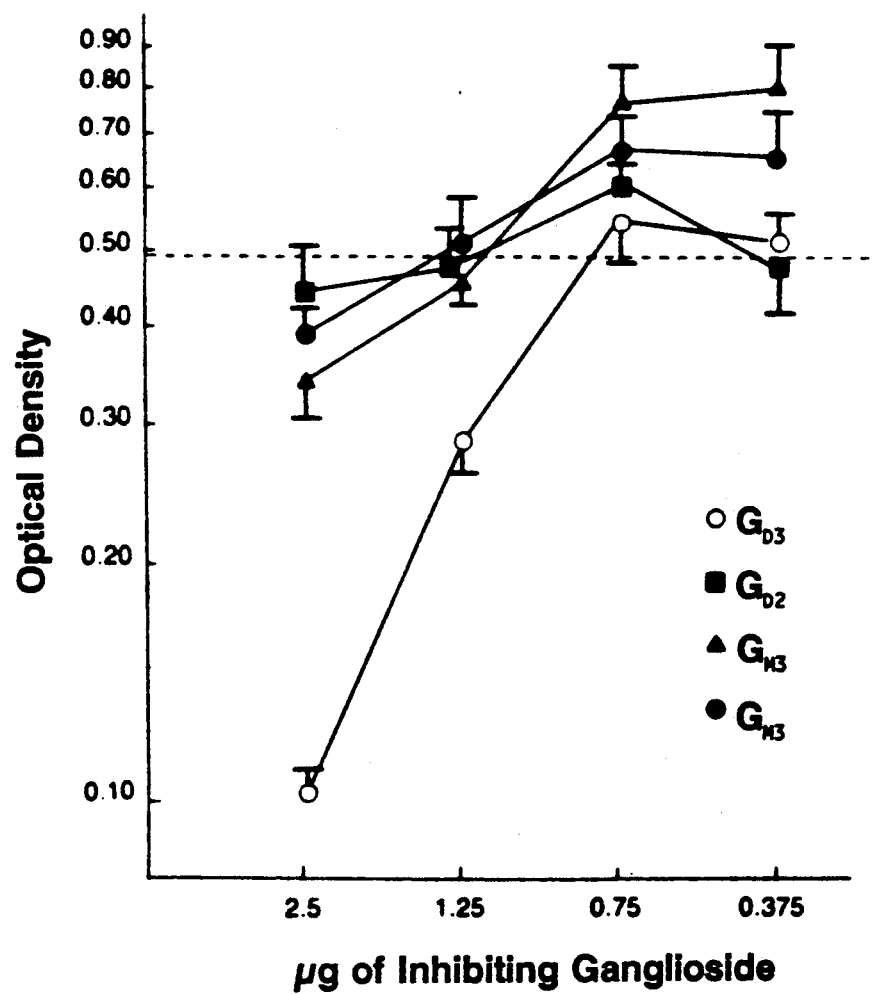
FIG. 3 shows inhibition by purified gangliosides of mAb R24 reactivity.

To confirm that mAb R24 was reacting with $G_{D3}$ rather than other components on the surface of T cells, we demonstrated that the antigenic determinant detected by mAb R24 had the characteristics of a ganglioside. MAb R24 reactivity with $E^+$ cells was destroyed by pretreating target cells with neuraminidase and ethanol, consistent with the properties of a sialylated glycolipid, but was unaffected by protease and trypsin. $G_{D3}$ was shown to be a minor ganglioside component of the acidic glycolipid preparations of peripheral blood $E^+$ cells stimulated with mAb R24 for 5 days (FIG. 2a). In stimulated $E^+$ cells, $G_{D3}$ comprises 3-5% of total gangliosides (FIG. 2b), while unstimulated $E^+$ cells contained lower levels of $G_{D3}$. MAb R24 reacted with a purified ganglioside fraction derived from peripheral blood T cells, and this reactivity was specifically inhibited by purified $G_{D3}$ but not b $G_{M2}$, $G_{M3}$ or $G_{D2}$ (FIG. 3). These results demonstrated that mAb R24 detected $G_{D3}$ ganglioside on T cells and that mAb R24 was not reacting with other gangliosides present in the T cell preparation. Finally, mAb R24 did not react with protein components from peripheral blood $E^+$ cells by Western blot analysis or by radioimmunoprecipitation of extracts labeled with 125I by the chloramine T method.

EXAMPLE III

MAb R24 Induces Proliferation of $E^+$ Lymphocytes

Figure 4:
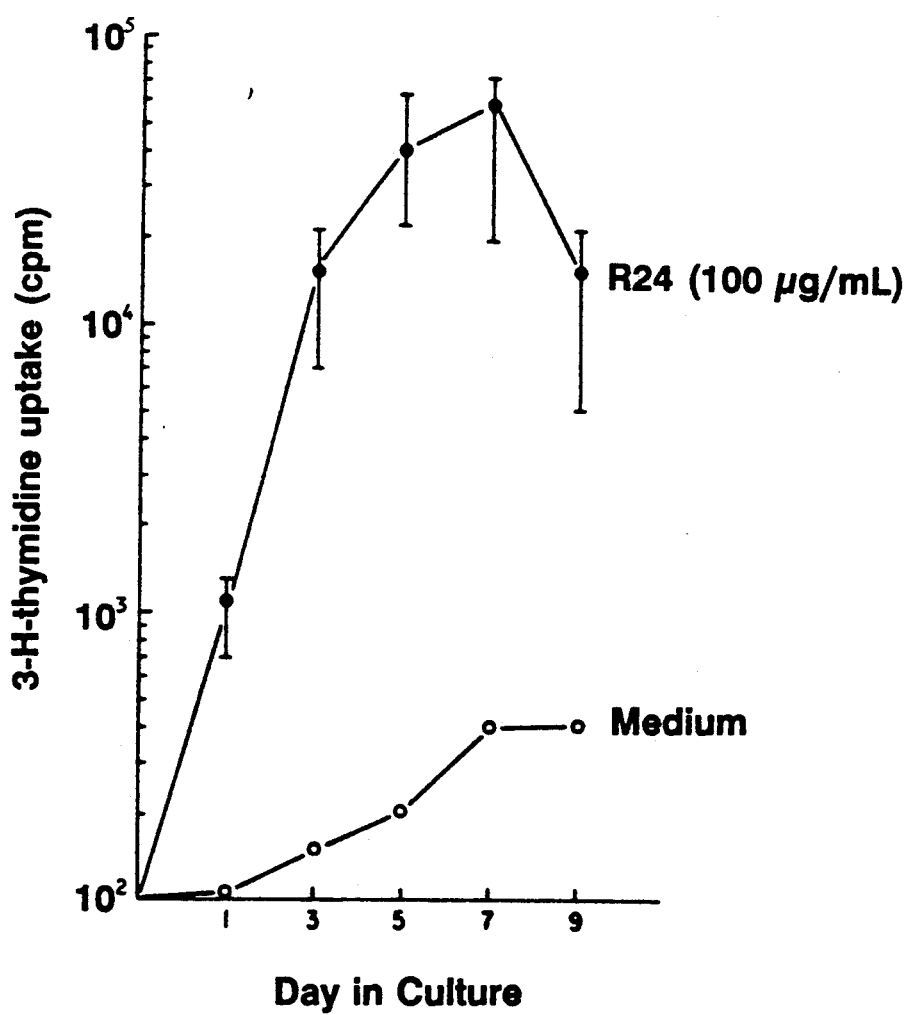
FIG. 4 shows proliferation of E+ lymphocytes with R24.

MAb R24 was found to stimulate the growth of both PBMC and $E^+$ cells. The kinetics of $^3H$-thymidine uptake by cells cultured in the presence of 100 ug/mL of mAB R24 are shown in FIG. 4. Maximum proliferation was observed after 5 to 7 days of stimulation. FIG. 5a shows the effect of various concentrations of mAb R24 on proliferation of $E^+$ cells between 2 and 5 days in culture. A dose-dependent response of proliferation was observed at all time points tested. A concentration of 20 ug/mL gave a significant increase of $^3H$-thymidine uptake over background (cultured in medium alone) at all days tested. At concentrations as low as 2 ug/mL, mAb R24 still produced a detectable increase in proliferation.

To establish that the stimulation of T cells was due specifically to antibody reacting with $G_{D3}$, we tested a second IgG3 antibody (mAb C5) and an IgM antibody (mAb K9) directed against $G_{D3}$. Both anti-$G_{D3}$ antibodies induced proliferation of T cells (Table 1) (Proliferation induced by mAb C5 was similar to results with mAb R24). Monoclonal antibodies recognizing other gangliosides, including an IgG3 against $G_{D2}$ and an IgM against $G_{M2}$, did not stimulate T cells. Likewise, a control IgG3 (mAb F36/22) that does not recognize gangliosides or react with T cells did not stimulate PBMC or E+ cells. We excluded the possibility that contaminating antibodies or substances (e.g. protein A) were responsible for the T cell stimulation. MAb R24 prepared by various methods induced similar levels of proliferation of E+ cells at equivalent protein concentrations. Stimulation was produced by supernatants from the R24 hybridoma, unpurified ascites from R24-hybridoma bearing mice, and ascites purified by ammonium sulfate precipitation with or without protein A affinity chromatography (Table 1). Protein A itself induced only minimal proliferation of E+ cells (2379±145 cpm $^3$H-thymmidine uptake at day 5 with 5 ug/mL protein A).

EXAMPLE IV

R24 F(ab')2 fragments stimulate T cells

To exclude the possibility that mAb R24 stimulated T cells through the Fc portion of the molecule, we isolated F(ab')2 fragments of mAb R24 by pepsin digestion. FIG. 5b demonstrates the uptake of $^3$H-thymidine of PBMC during stimulation by different concentrations (2, 20 and 200 ug/mL) of mAb R24 F(ab')2 fragments. Incubation of cells with F(ab')2 fragments of a control IgG3 monoclonal antibody mAb 3F8 (anti-$G_{D2}$) produced no increase in proliferation. The level of proliferation during stimulation with F(ab')2 fragments was one-half the level of proliferation induced by the same concentration of intact R24 antibody molecules (e.g., 30,000 cpm for 200 ug/mL of whole mAb R24 versus 18,000 cpm with 200 ug/mL of F(ab')2.

EXAMPLE V

MAb R24 Induces Production of IL-2 and Expression of the Receptor for IL-2

Production of IL-2 during stimulation of E+ cells by mAb R24 was detected in culture supernatants between 1 and 5 days (Table 2). By day 7 there was no measurable IL-2 in culture supernatants. The time course of IL-2 production was different from induction by other mitogens where IL-2 is produced during the first several days of stimulation (Welte, K., et al. (1983) J. Immunol. 131:2356). Table 2 details the percentage of IL-2 receptor-positive $E^{30}$ cells up to day 7 in culture. Expression of IL-2 receptor was detected by assays with monoclonal antibody, but high affinity and low affinity receptors were not distinguished. Results from three independent experiments performed with E+ cells from three different healthy donors showed that the percentage of IL-2 receptor positive cells rose from initially less than 3% to approximately 50% by day 7.

EXAMPLE VI

MAb R24 Stimulation Increases the proportion of R24+ Cells

Figure 6:
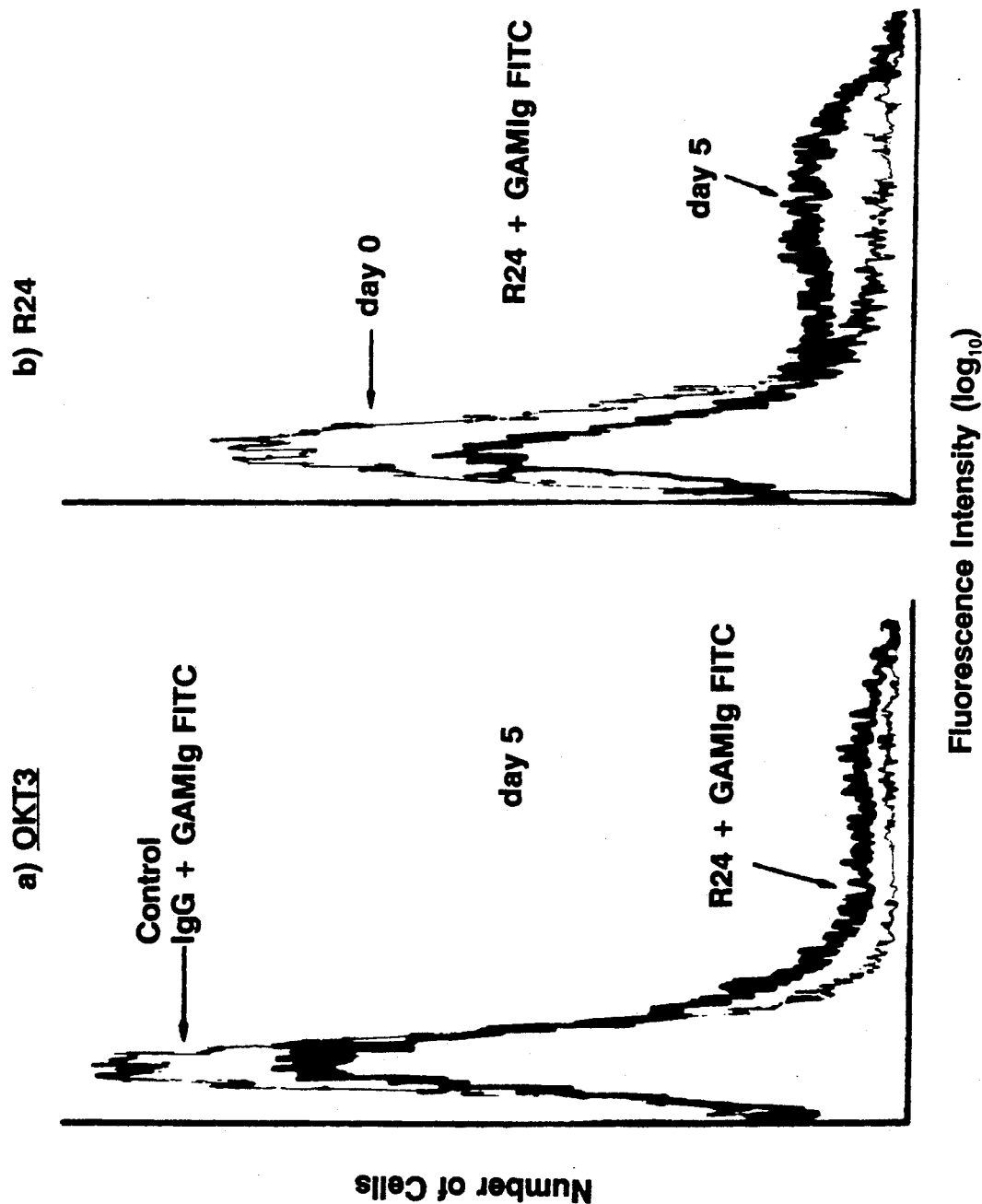
FIG. 6 shows flow-cytometer analysis of $E^{30}$ cells stimulated with anti-CD3 (OKT-3) antibody or R24.

Stimulation of $E^{30}$ cells and PBMC with mAb R24 produced an increase in the percentage of R24+ cells Sequential analysis of stimulated E+ cells by flow cytometry demonstrated that the proportion of R24+ cells rose significantly by days 5 to 7 (Table 1 and FIG. 6). The intensity of immunofluorescence staining by mAb R24 of stimulated cells is plotted in FIG. 6. The intensity of staining was heterogeneous; however, the brightest staining after stimulation was observed in large, blast-like cells when analyzed by 0± and 90° scatter by flow cytometry, suggesting that it was the R24 positive population of lymphocytes that was proliferating and expanding during stimulation. Analysis of PBMC resulted in similar percentages of R24 positive cells: 26% at day 2, 33% at day 3, 36% at day 5 and 39% at day 7. When anti-CD3 (OKT-3) antibody was used as a stimulator, the percentage of R24+ cells did not increase during 5 days of culture (FIG. 6).

EXAMPLE VII

Mitogenicity Induced by MAb R24 is Dependent on the Presence of R24+ Cells

Depletion of R25+ cells from the E+ cells by lysis with mAb R24 and human complement resulted in a reduction in the proliferation induced by mAb R24 (Table 3). The degree of decrease in proliferation was related to the concentration of mAb R24 used for complement-mediated lysis and the proportion of R24+ cells remaining in the culture. When lysis of R24+ cells was virtually complete, there was complete abrogation of stimulation of E+ cells by mAB R24.

EXAMPLE VIII

MAB R24-Induced Proliferation Occurs in Cultures Depleted of Macrophages

MAb R24 induced equivalent stimulation of PBMC cultures containing 10–20% macrophages and cultures of E+ cells depleted of macrophages (confirmed by flow cytometry analysis) as measured by expression of IL-2 receptors and level of cell proliferation (Table 4). PHA and anti-CD3 mAb, two mitogens that require accessory cells, did not stimulate these E+ cultures depleted of macrophages. When macrophages were added back to E+ cells (to 5% and 10% of the final cell number), there was no change in induction of proliferation by mAb R24 (Table 4).

EXAMPLE IX

Figure 7:
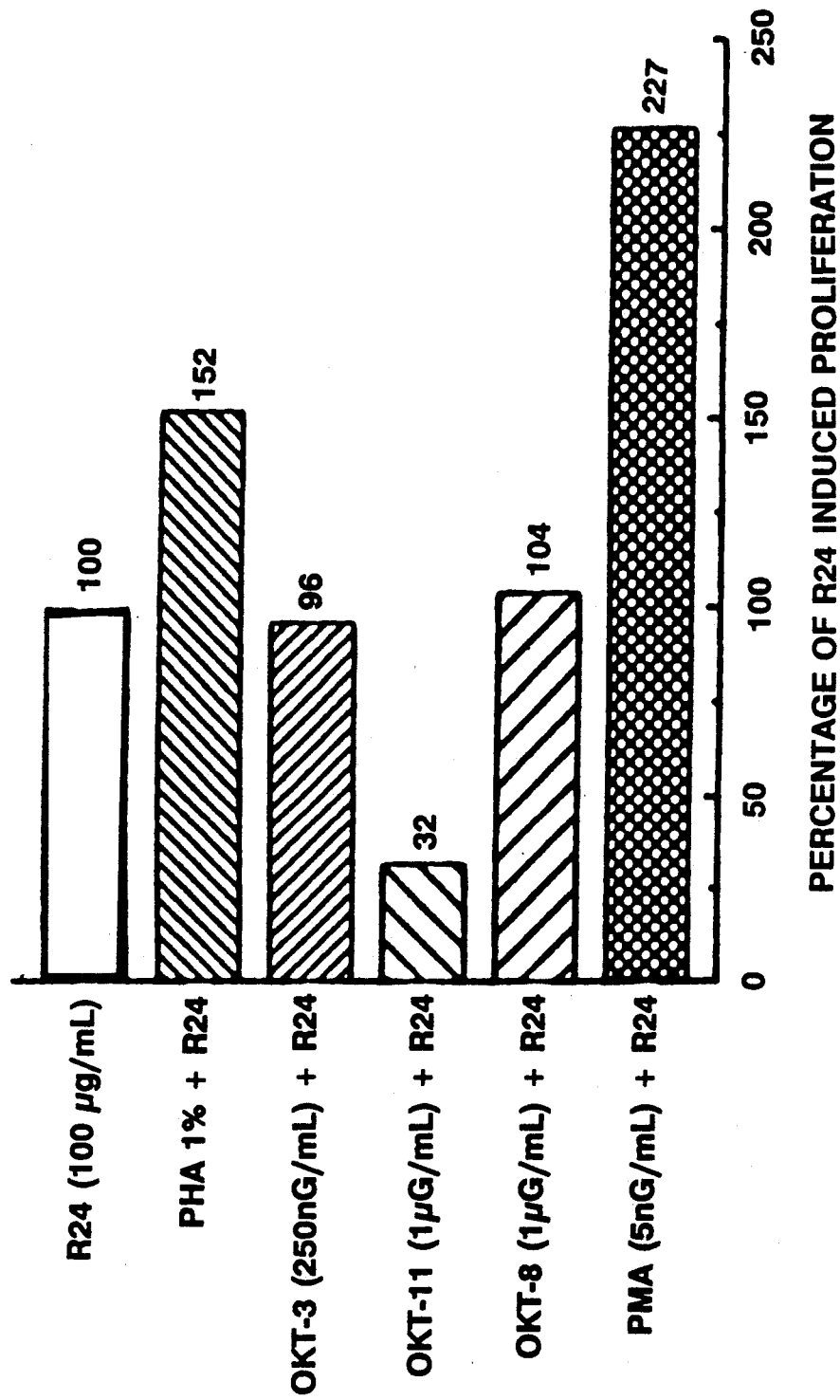
FIG. 7 shows effect of PHA, anti-T cell mAb and PMA on mAb R24 induced proliferation of $E^{30}$ cells.

Effects of Other T Cell Mitogens or Costimulators on MAb R24-Induced Stimulation of T Cells The potential influence of other established T cell mitogens on R24-induced proliferation of T cells was evaluated. FIG. 7 presents of representative experiments (at day 5 in culture). PHA at concentrations of 1% (v/v) increased R24-induced proliferations of E+ cells approximately 1.5 fold, while 1% PHA alone was minimally mitogenic (less than 10% of the level of proliferation achieved with 1% PHA in the presence of macrophages). Anti-CD3 (OKT-3) stimulation is also dependent on the presence of macrophages. Anti-CD3 at concentrations of 2.5 ng/mL, 25 ng/ML and 250 ng/mL did not augment or inhibit R24-induced stimulation of E+ cells depleted of macrophages (FIG. 7).

Anti-CD2 (OKT-11) did not induce stimulation of E+ cells when used alone, but anti-CD2 did inhibit mAB R24 induced proliferation (60% inhibition at 1 ug/mL and 33% inhibition at 100 ng/mL) (FIG. 7). Anti-CD8 (OKT-8), which is the same subclass as anti-CD2 and anti-CD3 and is known to inhibit IL-2 production and proliferation induced by anti-CD3 (Welte, K., et al. (1983) supra), did not inhibit or augment stimulation by mAb R24. The phorbol ester, PMA, a potent activator of protein kinase C (nishizuka, Y, (1986) Science 233:305) and a costimulator for anti-CD3 induced proliferation of monocyte-depleted T cells (Hara, T., et al. (1985) J. Exp. Med. 161:641), increases R24-induced proliferation by more than 2-fold (FIG. 7). The proliferation induced by mAb R24 as measured by $^3$H-thymidine uptake was the result of IL-2 production and IL-2 receptor expression (Table 1). To test whether exogenous IL-2 could increase mAb R24-induced proliferation, recombinant IL-2 (100 U/mL) was added to mAb R24-stimulated cultures. As shown in Table 5, exogenous IL-2 substantially increased the proliferation of E$^+$ cells when compared to stimulation by mAb R24 alone.

EXAMPLE X

It is shown here in Table 6 below that Protein A (recombinant material from Pharmacia Corp., Piscataway, N.J.) also increases proliferation of T cells and can serve as a stimulatory agent as shown.

TABLE 6

| Effect on Protein A on Lymphocyte Proliferation Proliferation ($^3$H - thymidine uptake day 3 in culture) | |
|---|---|
| Medium | 65 cpm |
| R 24 (100 ug/ml) | 17443 cpm |
| Protein A (5 ug/ml) | 2426 cpm |
| Protein A (0.5 ug/ml) | 1558 cpm |

In previous reports we have shown that the disialoganglioside $G_{D3}$ is expressed on cell types derived from the neuroectoderm, including melanocytes, adrenal medullary cells, glia, neurons, and islet cells of the pancreas (Real, F. X., et al. (1985) Cancer Res. 45:4401). With the finding that $G_{D3}$ is expressed by a subpopulation of thymocytes and peripheral blood lymphocytes, $G_{D3}$ joins a class of antigens which are shared by neuroectoderm-derived cells and cells of the immune system. Since both of these lineages are populated by cells whose primary function is cell-cell communication, it is possible that $G_{D3}$ may play a crucial role in cell signaling in these differentiation pathways. In the present study, we demonstrate that binding to $G_{D3}$ induces T cell activation, including the expression of IL-2 receptors, the production of IL-2 and cell proliferation. T cells can be stimulated by IgM, IgG and F(ab')$_2$ fragments that react with $G_{D3}$. These results are consistent with the interpretation that binding and cross-linking of $G_{D3}$ on the surface of T cells lead to a signal for activation.

As serum contains $G_{D3}$, it is possible that $G_{D3}$ on the surface of lymphocytes is the result of passive adsorption. However, several lines of evidence suggest that $G_{D3}$ is actively synthesized by T cells. First, $G_{D3}$ is selectively expressed at high levels by only a small subpopulation of T cells rather than by a broad population of cells. Second, the number of T cells expressing $G_{D3}$ increases substantially in tissue culture in the presence of anti-$G_{D3}$ antibodies. Third, $G_{D3}$ can be detected on T cell leukemia cell lines as well as fresh lymphocytic leukemia cells. In this regard, the level of $G_{D3}$ expression by the T cell leukemia cell line CEM has been shown to increase during stimulation with the phorbol ester PMA (Kiguchi, K., et al. (1986) Cancer Res. 46:3027).

Gangliosides have been shown to interact with signals and receptors that influence growth and differentiation of cells. Gangliosides added exogenously to growing cells have been found to alter binding affinity of growth factors to their receptors and to affect the state of tyrosine phosphorylation of growth factor receptors (Bremer, E. G., et al. (1984) J. Biol. Chem. 259:6818; Bremer, E. G., et al. (1986) J. Biol. Chem. 261:2434). A variety of glycoprotein molecules on the surface of T cells can mediate activation of T cells, including the IL-2 receptor, the Ti/CD3 molecular complex, and the CD2 antigen (Weiss, M.J., et al. (1984) Proc. Natl. Acad. Sci. USA 81:6836). Activation by these receptors generally requires accessory Fc receptor-positive cells such as macrophages and soluble components (e.g. IL-1) or PMA (Hara, T., et al. (1985) J. Exp. Med. 161:641). An exception is the CD2 receptor which is expressed early in T cell differentiation in the thymus (Meuer, S. C., et al. (1984) Cell 36:897). Activation by binding to $G_{D3}$, like CD2-mediated activation, does not appear to depend on accessory cells. Despite the diversity of cell surface receptors available for activation, only limited pathways appear to be available for transduction of signals inside the cell (Nishizuka, Y. (1986) Science 233:305; Imboden, J.B., et al. (1985) J. Exp. Med. 61:446). It is not clear whether $G_{D3}$ binding by mAb initiates activation at the level of known ligand-/surface receptors or through a separate, yet unidentified receptor complex. Several reports have suggested that extracellular gangliosides may bind IL-2, thereby inhibiting mitogen-induced proliferation of lymphocytes (Robb, R.J. (1986) J. Immunol. 136:971; Parker, J., et al. (1984) FEBS letters 170:391). In this case, gangliosides may compete for IL-2 reactivity by sequestering or inactivating IL-2. In addition to its possible reactivity with the soluble IL-2 molecule, Robb et al. (Robb, R. J. (1986) J. Immunol. 36:971) have shown that gangliosides are able to decrease the expression of IL-2 receptor (Tac antigen) on PHA-induced blasts. These results suggest that cellular gangliosides could be involved in the suppression of IL-2 receptor expression on resting T cells. In this model, binding of IL-2 or antibodies to critical gangliosides on T cells could permit full expression of IL-2 receptors. This would also be compatible with the observations that IL-2 is able to upregulate its own receptor (Reem, G. H., et al. (1984) Science 225:429; Welte, K., et al. (1984) J. Exp. Med. 160:1390) and that a prominent effect of mAb R24 on T cells is the induction of IL-2 receptor expression. This is also supported by the substantial increase in proliferation of mAb R24 stimulated E$^+$ cells in the presence of exogenous IL-2 (Table 5).

The stimulation of T cells by anti-$G_{D3}$ antibodies can be augmented by exogenous IL-2, PHA, and PMA, but not by anti-CD3 mAb. The inhibition of GD3-mediated activation by monoclonal antibodies to CD2 suggests that $G_{D3}$ might be associated with the CD3 molecule, but there are other possible explanations for this finding e.g. downregulation of CD3-mediated activation by binding to CD2 (Meuer, S. C., et al. (1983) Science 222:1239). $G_{D3}{}^+$ T cells appear to be essential for initial activation by mAb R24 since depletion of this population abrogates the proliferative response. Although it is possible that stimulation can lead to recruitment of $G_{D3}{}^-$ cells into the $G_{D3}{}^+$ population, it is more likely that activation by anti-$G_{D3}$ leads to expansion of the $G_{D3}{}^+$ pool of T cells: 1) $G_{D3}{}^+$ T cells are required for stimulation; 2) the expanding $G_{D3}{}^+$ pool is comprised mainly of proliferating, blast-like cells; and 3) stimulation by other mitogens such as PHA or anti-CD3 does not lead to a major increase in the proportion of $G_{D3}{}^+$ cells (FIG. 6). Experiments with cloned $G_{D3}{}^+$ and $G_{D3}{}^-$ T cell lines will help clarify this point and permit a functional analysis of $G_{D3}{}^+$ T cells. Experiments show mAb R24 does react with T3 lymphocytes and the proliferating population in R24 stimulated cultures includes a mixture of T4 and T8 lymphocytes.

MAb R24 can kill target cells by complement-mediated cytotoxicity and antibody-dependent cellular cytotoxicity. On the basis of the restricted reactivity and in vitro cytotoxic effects of mAb R24, a preliminary clinical trial was initiated to evaluate mAb R24 in the treatment of patients with metastatic melanoma (Houghton, A. N., et al. (1985) Proc. Natl. Acad. Sci. USA 82:1242). Intravenous infusion of mAb R24 induced clinical signs and symptoms of inflammation around tumors and regression or disappearance of lesions in some patients. There was evidence that treatment with mAb R24 produced complement deposition and infiltration of T cells (CD3+/CD8+/Ia+) in tumors. Although several biological properties of mAb R24 may contribute to its anti-tumor activity, the potential role of T cell activation is particularly intriguing. This view is supported by the finding of T cell infiltrates in regressing tumors after treatment with R24 but not in tumor biopsies prior to treatment. In addition, cytotoxic T cell clones have been established from a patient treated with R24. These T cell clones specifically kill autologous melanoma cells and not normal tissues or allogeneic melanomas. The possible activation of T cells in treated patients is a complex issue since mAb R24 can also lyse target T cells in the presence of human complement and thereby abolish T cell stimulation (Table 3). The ability of mAb R24 to lyse host T cells may partially explain the observation that tumor regressions have generally been seen only after treatment with low doses but not high doses of mAb R24 (Houghton, A.N., et al. (1985) Proc. Natl. Acad. Sci. USA 82:1242). It will be possible to investigate this issue since F(ab')2 fragments of mAb R24 can stimulate T cells but do not mediate complement lysis (P. Chapman, unpublished observation). F(ab')2 fragments will be investigated in a clinical trial in order to evaluate their potential role in cancer treatment.

One theory supposes a mAb "bridge" such that an arm of the R24 mAb binds to T cells and activates them while a different arm of the mAb binds to the tumor effecting killing.

Recombinant protein A is another stimulatory agent. For cancer treatment alone, Protein A can be either injected intravenously or blood can be removed from the body and passed over protein A and then reinfused (ex vivo). In each case in animal models, tumor regressions have been seen.

PHA or PMA use would most likely be in ex vivo treatment together with IL-2 and/or R24.

We also note the possibility of using F(ab')2 fragments ligated together with human immunoglobulin $F_c$ pieces in a chimeric antibody which might lead to improved tolerance for mAb R24 in patients.

Thus it is possible to either stimulation T cells directly in vivo which cells are then are guided to the tumor, or to stimulate a patients T cells outside the body as shown above and then inject these stimulated cells to effect tumor cytotoxicity in conjunction with added IL-2, Protein A, R24 etc.

The IL-2 range for treatment is approximately from a low dose of less than 1 million units to a high dose of greater than 3 million units of IL-2. A mid range is considered to be approximately 1-3 million units of IL-2.

TABLE 1

Analysis of T-Cell Stimulation by Monoclonal Antibodies Against Gangliosides

| MAb | MAb Concentration | $^3$H-Thymidine Incorporation[2] (CPM ± SD) |
|---|---|---|
| R24[1] | 100 μg/ml | 28497 ± 6501 |
| R24[1] | 30 μg/ml | 5390 ± 536 |
| R24 hybridoma supernatant | 30 μg/ml | 4899 ± 951 |
| K9 (IgM, anti-$G_{D3}$) | 100 μg/ml | 10777 ± 3982 |
| 10-11 (IgM, anti-$G_{M2}$) | 100 μg/ml | 565 ± 186 |
| 3F8 (IgG3, anti-$G_{D2}$) | 100 μg/ml | 610 ± 79 |
| F36/22 (IgG3 control) | 100 μg/ml | 1137 ± 55 |
| Medium | — | 733 ± 415 |

[1]Purified from Ascites
[2]5 days in culture

TABLE 2

IL-2 Production, IL-2 Receptor and $G_{D3}$ Expression by E+ Cells Stimulated with MAb R24

| Day of Stimulation | IL-2 Production (U/mL ± SD)[1] | IL-2 Receptor Positive Cells (% Positive ± SD)[1] | R24+ Cells (% Positive) |
|---|---|---|---|
| 0 | 0 | <3 | 9.9[2] |
| 1 | 1.4 ± 1.2 | 6.6 ± 2.0 | 15.9 |
| 2 | 1.3 | 12.8 ± 8.0 | 21.6 |
| 3 | 0.9 ± 0.3 | 22.3 ± 11 | 25.9 |
| 5 | 0.7 ± 0.5 | 38.9 ± 7.5 | 44.0[2] |
| 7 | 0 | 49.7 ± 4.5 | 43.0 |

[1]Results from 3 independent experiments (with the exception of a single measurement of IL-2 production on day 2) using mAb R24 (100 μg/ml) for stimulation
[2]Also shown in FIG. 6

TABLE 3

R24-Induced Proliferation of E+ Cells after Complement-Mediated Depletion of R24+ Cells[1]

| | E+ Cells After Treatment | | |
|---|---|---|---|
| | | $^3$H-Thymidine Uptake (CPM) | |
| E+ Cells Treated with | % R24+ | Day 3 | Day 5 |
| R24 (100 μg/mL) + Complement | <1 | 55 | 36 |
| R24 (10 μg/mL) + Complement | 3 | 320 | 1729 |
| R24 (1 μg/mL) + Complement | 7 | 977 | 4138 |
| Complement Alone | 15 | 4942 | 31330 |
| R24 (100 μg/mL) + Alone | 15 | 4656 | 25069 |

[1]E+ cells were treated with or without mAb R24/complement (see Materials and Methods), assayed for percentage R24+ cells and then stimulated with mAb R24 (100 μg/mL).

TABLE 4

Effect of Macrophage Depletion on MAb R24-Induced Proliferation of E+ Cells

| Cell Fraction | $^3$H-Thymidine Incorporation (CPM) |
|---|---|
| Exp. 1 | |
| E+ | 7235 ± 775 |
| E+ + 5% Macrophages | 5341 ± 729 |
| E+ + 10% Macrophages | 7486 ± 1301 |
| Exp. 2 | |
| E+ | 15076 ± 631 |
| PBMC | 12240 ± 710 |

[1]3 days in culture stimulated with mAb R24 (100 ug/ml)
Results are shown as mean and standard deviation of triplicate cultures.

TABLE 5

Effect of Exogenous IL-2 on Proliferation of E+ Cells Induced by MAb R24

| Day of Stimulation | R24 Alone[1] | R24 + IL-2[2] | Fold Increase |
|---|---|---|---|
| 3 | 17672 ± 325 | 27710 ± 2356 | 1.6 |

TABLE 5-continued

Effect of Exogenous IL-2 on Proliferation of E+ Cells Induced by MAb R24

| Day of Stimulation | R24 Alone[1] | R24 + IL-2[2] | Fold Increase |
|---|---|---|---|
| 5 | 25069 ± 1041 | 104402 ± 2038 | 4.2 |
| 7 | 16667 ± 2442 | 98007 ± 10373 | 5.9 |
| 9 | 4461 ± 930 | 45573 ± 2443 | 10.2 |

[1] MAb R24 100 μg/ml
[2] MAb R24 100 μg/ml plus IL-2 100 U/ml. Maximum $^3$H-thymidine uptake in the presence of IL-2 alone was 25361 ± 11705 CPM at day 7 of culture. Results are shown as mean and standard deviation of triplicate cultures.

What is claimed is:

1. A composition for treating melanoma in humans consisting essentially of a monoclonal antibody which reacts immunologically with $G_{D3}$ ganglioside and IL-2 in physiologically active amounts.

2. A composition of claim 1 wherein the monoclonal antibody comprises an IgG antibody.

3. A composition for treating melanoma in humans consisting essentially of the F(ab')$_2$ fragment of a monoclonal antibody which reacts immunogolically with $G_{D3}$ ganglioside and IL-2 in physiologically active amounts.

4. A composition of claim 1 wherein the monoclonal antibody is R24 and is produced by hybridoma M-18 (R24), deposited with ATCC under Accession No. HB 8445.

5. A composition of claim 3, wherein the monoclonal antibody is R24 and is produced by hybridoma M-18, deposited with ATCC under Accession No. HB 8445.

6. A method for treating melanoma in humans which comprises exposing melanoma patients or their peripheral blood mononuclear leukocytes to the composition of claim 1.

7. A method for treating melanoma in humans which comprises exposing melanoma patients or their peripheral blood mononuclear leukocytes to the composition of claim 3.

8. A method for treating melanoma in humans which comprises exposing melanoma patients or their peripheral blood mononuclear leukocytes to the composition of claim 4.

9. A method for treating melanoma in humans which comprises exposing melanoma patients or their peripheral blood mononuclear leukocytes to the composition of claim 5.

* * * * *